US009914145B2

(12) United States Patent
Osborn et al.

(10) Patent No.: US 9,914,145 B2
(45) Date of Patent: Mar. 13, 2018

(54) DIFFUSER AND RELATED METHODS

(71) Applicant: Scentsy, Inc., Meridian, ID (US)

(72) Inventors: Warren Osborn, Provo, UT (US);
Bryce Fisher, Provo, UT (US); Diogo Myrrha, Provo, UT (US); Ephraim Sng, Provo, UT (US); Ezra Kwong, Pleasant Grove, UT (US); Mark Sullivan, Sandy, UT (US)

(73) Assignee: Scentsy, Inc., Meridian, ID (US)

( * ) Notice: Subject to any disclaimer, the term of this patent is extended or adjusted under 35 U.S.C. 154(b) by 0 days.

(21) Appl. No.: 15/141,572

(22) Filed: Apr. 28, 2016

(65) Prior Publication Data
US 2016/0318059 A1 Nov. 3, 2016

Related U.S. Application Data

(63) Continuation of application No. 62/154,574, filed on Apr. 29, 2015.

(51) Int. Cl.
*B05B 17/06* (2006.01)
*A61L 9/12* (2006.01)
(Continued)

(52) U.S. Cl.
CPC .......... *B05B 17/0615* (2013.01); *A61L 9/122* (2013.01); *A61L 9/14* (2013.01);
(Continued)

(58) Field of Classification Search
CPC ............ B05B 17/0615; B05B 17/0653; B05B 17/0607; B05B 7/2416; A61L 9/122; A61L 9/14; A61L 2209/132
(Continued)

(56) References Cited

U.S. PATENT DOCUMENTS 3,901,443 A * 8/1975 Mitsui ................ B05B 17/0615
239/102.2
3,970,250 A * 7/1976 Drews .................. A61M 11/005
128/200.16
(Continued)

FOREIGN PATENT DOCUMENTS

EP 1150779 B1 6/2004
EP 1159078 B1 12/2004
(Continued)

OTHER PUBLICATIONS

European Search Report from European Application No. 16 16 6080, dated Sep. 23, 2016, 6 pages.

*Primary Examiner* — Arthur O Hall
*Assistant Examiner* — Joseph A Greenlund
(74) *Attorney, Agent, or Firm* — TraskBritt (57) ABSTRACT

A liquid diffuser includes a base, a liquid reservoir, a spout for resting on the reservoir and having an upper opening, a fan, a polymeric gasket encircling the liquid reservoir, and a cover. The gasket includes a flange extending over a portion of an upper surface of the base that extends laterally beyond the liquid reservoir. The cover is sized and configured to be positioned over and around the liquid reservoir and the spout, and to rest upon the flange of the gasket. Methods of assembling such a liquid diffuser include resting the spout upon the liquid reservoir, and resting the spout upon the flange of the gasket over the base. Method of using such a liquid diffuser include powering a transducer for generating atomized droplets of the liquid, and supplying power to the fan to carry the atomized droplets of the liquid out from the diffuser with forced airflow.

19 Claims, 11 Drawing Sheets

(51) Int. Cl.
*A61L 9/14* (2006.01)
*F21V 29/67* (2015.01)
*F21V 29/74* (2015.01)
*B05B 7/24* (2006.01)
*F21V 33/00* (2006.01)
*F21Y 101/00* (2016.01)
*F21Y 115/10* (2016.01)

(52) U.S. Cl.
CPC ........ *B05B 7/2416* (2013.01); *B05B 17/0653* (2013.01); *F21V 29/67* (2015.01); *F21V 29/74* (2015.01); *F21V 33/0004* (2013.01); *B05B 17/0607* (2013.01); *F21Y 2101/00* (2013.01); *F21Y 2115/10* (2016.08)

(58) Field of Classification Search
USPC ............. 239/4, 102.1, 102.2, 338, 340, 369; 422/123–124
See application file for complete search history.

(56) References Cited

U.S. PATENT DOCUMENTS

| | | | |
|---|---|---|---|
| 5,464,572 A * | 11/1995 | Bonzi | B05B 17/0615 250/324 |
| 6,293,474 B1 | 9/2001 | Helf et al. | |
| 6,378,780 B1 | 4/2002 | Martens, III et al. | |
| 7,687,744 B2 * | 3/2010 | Walter | A61L 9/037 219/494 |
| 7,744,232 B2 | 6/2010 | Gruenbacher et al. | |
| 7,963,460 B2 * | 6/2011 | Jorgensen | A61L 9/122 239/102.1 |
| 7,992,801 B2 * | 8/2011 | Jorgensen | A61L 9/03 239/102.1 |
| 8,133,440 B2 * | 3/2012 | Jorgensen | A61L 9/14 239/34 |
| 8,196,903 B2 * | 6/2012 | Jorgensen | A61L 9/14 239/102.1 |
| 8,491,843 B2 | 7/2013 | Spano, Jr. et al. | |
| 8,602,396 B1 | 12/2013 | V et al. | |
| 8,770,557 B2 | 7/2014 | Kanel | |
| 9,078,938 B2 * | 7/2015 | Hsiao | A61L 9/14 |
| 9,278,365 B2 * | 3/2016 | Banco | B05B 7/2491 |
| D755,361 S * | 5/2016 | Osborn | D23/366 |
| 2001/0042794 A1 | 11/2001 | Tomkins et al. | |
| 2004/0022675 A1* | 2/2004 | An | A61L 9/02 422/29 |
| 2005/0185398 A1 | 8/2005 | Scannell | |
| 2006/0188238 A1 | 8/2006 | Kent | |
| 2007/0230189 A1 | 10/2007 | Gruenbacher et al. | |
| 2007/0237498 A1 | 10/2007 | Helf et al. | |
| 2008/0041972 A1* | 2/2008 | Chen | B05B 17/0646 239/102.2 |
| 2008/0099572 A1 | 5/2008 | Tollens et al. | |
| 2008/0135640 A1 | 6/2008 | Velazquez et al. | |
| 2008/0138051 A1 | 6/2008 | Velazquez et al. | |
| 2008/0223953 A1* | 9/2008 | Tomono | A01M 1/205 239/102.2 |
| 2008/0245362 A1* | 10/2008 | Moessis | A61M 15/0085 128/200.16 |
| 2009/0224064 A1 | 9/2009 | Brodbeck et al. | |
| 2010/0220464 A1 | 9/2010 | Gruenbacher | |
| 2011/0024521 A1* | 2/2011 | Jorgensen | B05B 17/0615 239/102.1 |
| 2011/0049266 A1 | 3/2011 | Jorgensen | |
| 2011/0221078 A1* | 9/2011 | Lev | A61L 9/03 261/81 |
| 2012/0145255 A1 | 6/2012 | Spano, Jr. et al. | |
| 2012/0251296 A1* | 10/2012 | Jorgensen | B05B 17/0607 415/116 |
| 2013/0010478 A1 | 1/2013 | Hasenoehrl et al. | |
| 2013/0175362 A1* | 7/2013 | Lee | F24F 6/14 239/302 |
| 2014/0103479 A1* | 4/2014 | Luc | A61L 9/12 257/435 |
| 2014/0158129 A1 | 6/2014 | Pratt, Jr. et al. | |

FOREIGN PATENT DOCUMENTS

| | | |
|---|---|---|
| EP | 1159077 B1 | 5/2008 |
| EP | 2347773 A1 | 7/2011 |
| EP | 2384771 A1 | 11/2011 |
| EP | 2086314 B1 | 8/2012 |
| EP | 2384771 B1 | 1/2013 |
| EP | 1430958 B1 | 4/2013 |
| EP | 2767301 A1 | 8/2014 |
| GB | 2473290 A | 3/2011 |
| JP | 2002126067 | 5/2002 |
| JP | 2004159875 | 6/2004 |
| JP | 2004321497 | 11/2004 |
| JP | 2005296540 | 10/2005 |
| JP | 4018730 | 12/2007 |
| JP | 2009233530 | 10/2009 |
| JP | 2011167478 | 9/2011 |
| JP | 2012196615 | 10/2012 |
| JP | 2012523303 | 10/2012 |
| JP | 201324479 | 2/2013 |
| JP | 201324480 | 2/2013 |
| JP | 5175263 | 4/2013 |
| JP | 5319948 | 10/2013 |
| JP | 2013230308 | 11/2013 |
| JP | 2013255920 | 12/2013 |
| JP | 5382071 | 1/2014 |
| JP | 5516526 | 6/2014 |
| WO | 2006112590 | 10/2006 |
| WO | 2012078973 | 6/2012 |
| WO | 2014003260 | 1/2014 |
| WO | 2014062378 | 4/2014 |

* cited by examiner

DIFFUSER AND RELATED METHODS

CROSS-REFERENCE TO RELATED APPLICATION

This application claims the benefit of U.S. Provisional Patent Application Ser. No. 62/154,574, filed Apr. 29, 2015, the disclosure of which is hereby incorporated herein in its entirety by this reference.

TECHNICAL FIELD

Embodiments of the present disclosure relate generally to diffusers for diffusing liquids into the ambient air, and to methods of assembling and using such diffusers.

BACKGROUND

Diffusers are devices that are used to generate atomized droplets of liquids and to disperse the atomized droplets of liquid into the ambient air surrounding the diffuser. For example, some diffusers are used for humidification. Diffusers are also used for aromatherapy, wherein scented oils or other therapeutic liquids are atomized and dispensed into the surrounding ambient air. Diffusers often employ an ultrasonic transducer to generate ultrasonic vibrations in a bath of liquid held within the diffuser. A fan is used to generate airflow through the diffuser, the airflow carrying the atomized droplets of liquid generated by the ultrasonic transducer out from the diffuser and into the surrounding ambient air.

BRIEF SUMMARY

In some embodiments, the present disclosure includes a diffuser for diffusing liquid into surrounding ambient air. The diffuser includes a base member, an ultrasonic transducer, a liquid reservoir, a spout, a fan, a polymeric gasket, and a cover. The base member has an upper surface and a lower surface. The ultrasonic transducer is mounted to the base member over the upper surface thereof. The liquid reservoir is mounted to the base member over the upper surface thereof. The liquid reservoir has surfaces defining a receptacle for holding a volume of liquid therein. At least a portion of an upper surface of the base member extends laterally beyond an outer peripheral side surface of the liquid reservoir. The liquid reservoir includes a bottom wall and at least one vertically extending sidewall. At least a surface of the ultrasonic transducer is exposed to any volume of liquid held within the receptacle such that ultrasonic vibrations of the ultrasonic transducer generate atomized droplets of the liquid over the volume of liquid held within the reservoir.

The spout is sized and configured to rest upon the liquid reservoir and includes an opening at an upper end thereof. The fan is mounted to the base member and configured to force airflow from the exterior of the diffuser, into the base member, around the receptacle in the liquid reservoir, into a volume of space enclosed by the spout and the liquid reservoir overlying any volume of liquid held within the receptacle, and out through the opening at the upper end of the spout to the ambient air external the diffuser. The forced airflow carries the atomized droplets of the liquid generated by the ultrasonic transducer to the exterior of the diffuser through the opening at the upper end of the spout.

The polymeric gasket encircles the liquid reservoir and includes at least one flange that extends at least partially over the portion of the upper surface of the base member extending laterally beyond the outer peripheral side surface of the liquid reservoir.

The cover is sized and configured to be positioned over and around the liquid reservoir and the spout, and to rest upon the at least one flange of the polymeric gasket such that the at least one flange is disposed between the cover and the portion of the upper surface of the base member extending laterally beyond the outer peripheral side surface of the liquid reservoir. The cover includes at least one opening at an upper end thereof such that the forced airflow generated by the fan passes through the opening at the upper end of the cover.

In additional embodiments, the present disclosure includes methods of assembling such a liquid diffuser. For example, a structure may be provided that includes a base member, an ultrasonic transducer, a liquid reservoir, a fan, and a polymeric gasket. The base member has an upper surface and a lower surface, and the ultrasonic transducer is mounted to the base member over the upper surface thereof. The liquid reservoir is mounted to the base member over the upper surface thereof. The liquid reservoir has surfaces defining a receptacle for holding a volume of liquid therein. At least a portion of an upper surface of the base member extends laterally beyond an outer peripheral side surface of the liquid reservoir. The liquid reservoir includes a bottom wall and at least one vertically extending sidewall. At least a surface of the ultrasonic transducer is exposed to any volume of liquid held within the receptacle such that ultrasonic vibrations of the ultrasonic transducer generate atomized droplets of the liquid over the volume of liquid held within the reservoir. The fan is mounted to the base member and configured to force airflow from the exterior of the diffuser, into the base member, and around the receptacle in the liquid reservoir. The forced airflow carries the atomized droplets of the liquid generated by the ultrasonic transducer to the exterior of the diffuser. The polymeric gasket encircles the liquid reservoir and includes at least one flange that extends at least partially over the portion of the upper surface of the base member extending laterally beyond the outer peripheral side surface of the liquid reservoir.

After providing such a structure, a spout is rested upon the liquid reservoir. The spout includes an opening at an upper end thereof and encloses a volume of space between the spout and the liquid reservoir.

A cover is then positioned over and around the liquid reservoir, and the spout is rested upon the at least one flange of the polymeric gasket such that the at least one flange is disposed between the cover and the portion of the upper surface of the base member extending laterally beyond the outer peripheral side surface of the liquid reservoir. The cover includes at least one opening at an upper end thereof such that the forced airflow generated by the fan passes through the opening at the upper end of the cover.

In yet further embodiments, the present disclosure includes methods of using a liquid diffuser. For example, a liquid diffuser is provided that includes a base member, an ultrasonic transducer, a liquid reservoir, a spout, a fan, a polymeric gasket, and a cover. The base member has an upper surface and a lower surface. The ultrasonic transducer is mounted to the base member over the upper surface thereof. The liquid reservoir is mounted to the base member over the upper surface thereof. The liquid reservoir has surfaces defining a receptacle for holding a volume of liquid therein. At least a portion of an upper surface of the base member extends laterally beyond an outer peripheral side surface of the liquid reservoir. The liquid reservoir includes a bottom wall and at least one vertically extending sidewall. At least a surface of the ultrasonic transducer is exposed to any volume of liquid held within the receptacle. The spout is sized and configured to rest upon the liquid reservoir and includes an opening at an upper end thereof. The fan is mounted to the base member. The polymeric gasket encircles the liquid reservoir and includes at least one flange that extends at least partially over the portion of the upper surface of the base member extending laterally beyond the outer peripheral side surface of the liquid reservoir. The cover includes at least one opening at an upper end thereof.

After providing the liquid diffuser, a volume of liquid is provided in the receptacle of the liquid reservoir. The spout is then rested upon the liquid reservoir, and the cover is positioned over and around the liquid reservoir and the spout and rested upon the at least one flange of the polymeric gasket such that the at least one flange is disposed between the cover and the portion of the upper surface of the base member extending laterally beyond the outer peripheral side surface of the liquid reservoir.

Power is then supplied to the ultrasonic transducer and atomized droplets of the liquid are generated over the volume of liquid held within the reservoir by ultrasonic vibrations of the ultrasonic transducer. Power is also supplied to the fan such that the fan forces airflow from the exterior of the diffuser, into the base member, around the receptacle in the liquid reservoir, into a volume of space enclosed by the spout and the liquid reservoir overlying the volume of liquid held within the receptacle, and out through the opening at the upper end of the spout to the ambient air external the diffuser. The forced airflow carries the atomized droplets of the liquid generated by the ultrasonic transducer to the exterior of the diffuser through the opening at the upper end of the spout.

BRIEF DESCRIPTION OF THE DRAWINGS

FIG. 1 is a perspective view of a diffuser for diffusing liquid into surrounding ambient air according to an embodiment of the present disclosure.

FIG. 2A is a cross-sectional side view of the diffuser of FIG. 1.

FIG. 2B is identical to FIG. 2A, but does not include reference characters, and illustrates cut-away planes of the views of FIGS. 3 through 6.

FIG. 3 is a perspective view of the diffuser of FIG. 1, cut-away along plane 3-3 in FIG. 1.

FIG. 4 is a perspective view of the diffuser of FIG. 1, cut-away along plane 4-4 in FIG. 1.

FIG. 5 is a perspective view of the diffuser of FIG. 1, cut-away along plane 5-5 in FIG. 1.

FIG. 6 is a perspective view of the diffuser of FIG. 1, cut-away along plane 6-6 in FIG. 1.

FIG. 7 is a front side view of the diffuser illustrating a polymeric gasket of the diffuser positioned around a liquid reservoir of the diffuser.

FIG. 8A is a perspective view of the polymeric gasket shown in FIG. 7.

FIG. 8B is a side view of the polymeric gasket of FIG. 8A.

FIGS. 9A and 9B are perspective views of a liquid reservoir of the diffuser of FIG. 1.

FIG. 10A is a cross-sectional side view of a spout of the diffuser of FIG. 1 separate from the other components of the diffuser.

FIG. 10B is a bottom view of the spout of FIG. 10A.

FIG. 11 illustrates a decorative cover positioned over and around the diffuser of FIG. 1.

DETAILED DESCRIPTION

The illustrations presented herein are not meant to be actual views of any particular diffuser, component thereof, or method, but are merely idealized representations which are employed to describe certain embodiments of the present disclosure. For clarity in description, various features and elements common among the illustrated embodiments may be referenced with the same or similar reference numerals.

As used herein, any directional term (e.g., upper, lower, side, top, bottom, etc.) refers to a direction relative to the diffuser when the diffuser is used during normal operation. By way of non-limiting example, an upper portion of a diffuser is the upper portion while the diffuser is placed on a surface in an orientation for use, and used to diffuse liquid into the ambient air.

FIG. 1 illustrates a diffuser 100 for diffusing liquid into surrounding ambient air. The diffuser 100 includes a base member 102, a liquid reservoir 104 mounted to the base member 102, and a spout 106 sized and configured to rest upon the liquid reservoir 104. The spout 106 includes an opening 108 at an upper end 110 thereof, through which air and atomized droplets of liquid carried by the air are expelled out from the diffuser 100 into the surrounding ambient air.

FIG. 2A is a cross-sectional side view of the diffuser 100. As shown therein, the base member 102 has an upper surface 112 and a lower surface 114. The liquid reservoir 104 is mounted to the base member 102 over the upper surface 112 thereof. As shown in FIG. 2A, at least a portion 118 of the upper surface 112 of the base member 102 may extend laterally beyond an outer peripheral side surface 120 of the liquid reservoir 104. This portion 118 may allow a decorative cover to rest upon the portion 118 of the upper surface 112 of the base member 102, as discussed in further detail subsequently herein.

As shown in FIG. 2A, the liquid reservoir 104 has surfaces defining a receptacle 116 for holding a volume of liquid therein. For example, the liquid reservoir 104 may include a bottom wall 122 and at least one vertically extending sidewall 124. An inner surface of the sidewall 124 and an upper surface of the bottom wall 122 may define the receptacle 116 for holding liquid. The bottom wall 122 may not be flat, and may taper to a lowermost point on the upper surface of the bottom wall 122 so as to funnel fluid held within the receptacle 116 toward the lowermost point on the upper surface of the bottom wall 122. The liquid reservoir 104 may include an exterior sidewall 138 extending upwardly from the base member 102 and adjoining an upper end of the at least one vertically extending sidewall 124 of the liquid reservoir 104.

The diffuser 100 further includes an ultrasonic transducer 126 mounted to the base member 102 over the upper surface thereof. The ultrasonic transducer 126 is shown in FIGS. 2A and 5. As shown in FIG. 2A, the ultrasonic transducer 126 may be indirectly mounted to the base member 102 by way of the liquid reservoir 104. For example, the ultrasonic transducer 126 may be mounted to the liquid reservoir 104 at a lower end thereof. The bottom wall 122 of the liquid reservoir 104 may have an aperture 128 formed therethrough at the lowermost point of the bottom wall 122. A surface of the ultrasonic transducer 126 may be exposed at the bottom of the aperture 128, such that the surface of the ultrasonic transducer 126 is exposed to any volume of liquid held within the receptacle 116. The ultrasonic transducer 126 converts electrical energy into ultrasonic mechanical vibrations. In particular, the exposed surface of the ultrasonic transducer 126 may vibrate at ultrasonic frequencies during operation of the diffuser 100. The ultrasonic vibrations of the ultrasonic transducer 126 generate atomized droplets of the liquid held within the receptacle 116. The atomized droplets of the liquid may be generated over the surface of the volume of liquid held within the liquid reservoir 104.

Figure 2A:
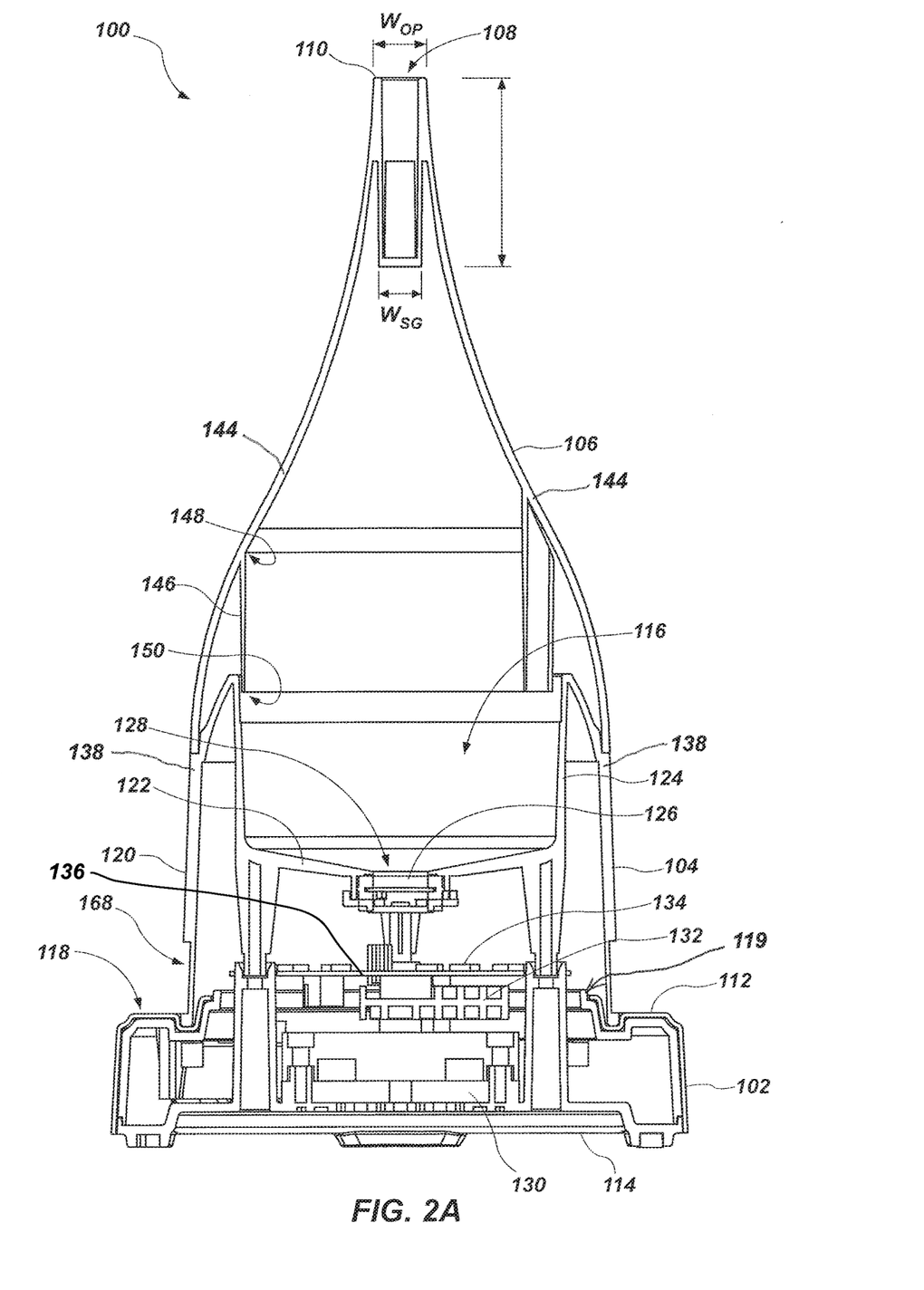
Figure 3:
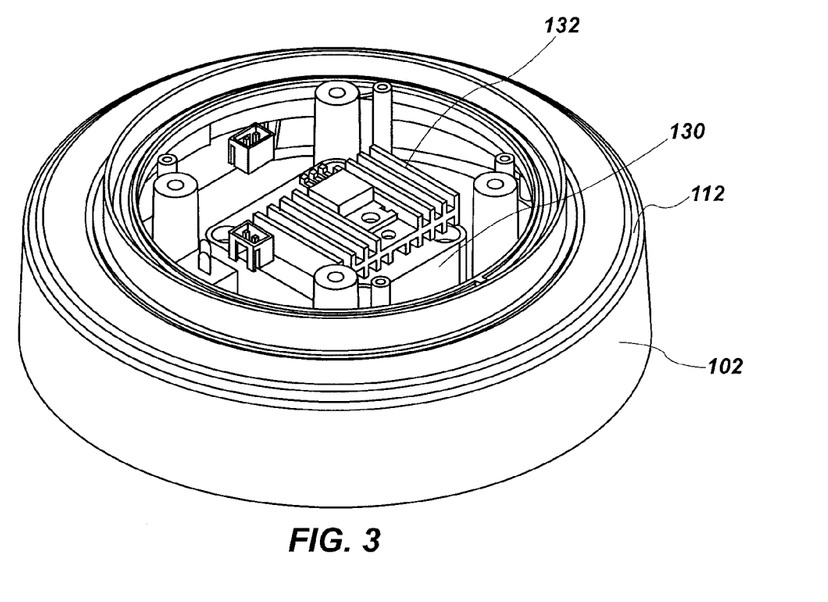

As shown in FIGS. 2A and 3, the diffuser 100 includes a fan 130. The fan 130 is mounted to the base member 102, and is configured to force airflow from the exterior of the diffuser 100, into the base member 102, around the receptacle 116 in the liquid reservoir 104, into a volume of space enclosed by the spout 106 and the liquid reservoir 104 overlying any volume of liquid held within the receptacle 116, and out through the opening 108 at the upper end 110 of the spout 106 to the ambient air external to the diffuser 100. The forced airflow driven by the fan 130 carries the atomized droplets of the liquid generated by the ultrasonic transducer 126 to the exterior of the diffuser 100 through the opening 108 at the upper end 110 of the spout 106. For example, one or more apertures may be formed through the lower wall of the base member 102 vertically below the fan 130, and the air outside the diffuser 100 may be drawn into the base member 102 by the fan 130 through the apertures in the lower wall of the base member 102. The exterior sidewall 138 of the liquid reservoir 104 may have at least one aperture 140 extending therethrough to allow the forced airflow generated by the fan 130 to pass from a space between the base member 102 and the liquid reservoir 104, around the receptacle 116, and into the volume of space enclosed by the spout 106 and the liquid reservoir 104 overlying any volume of liquid held within the receptacle 116.

Figure 9A:
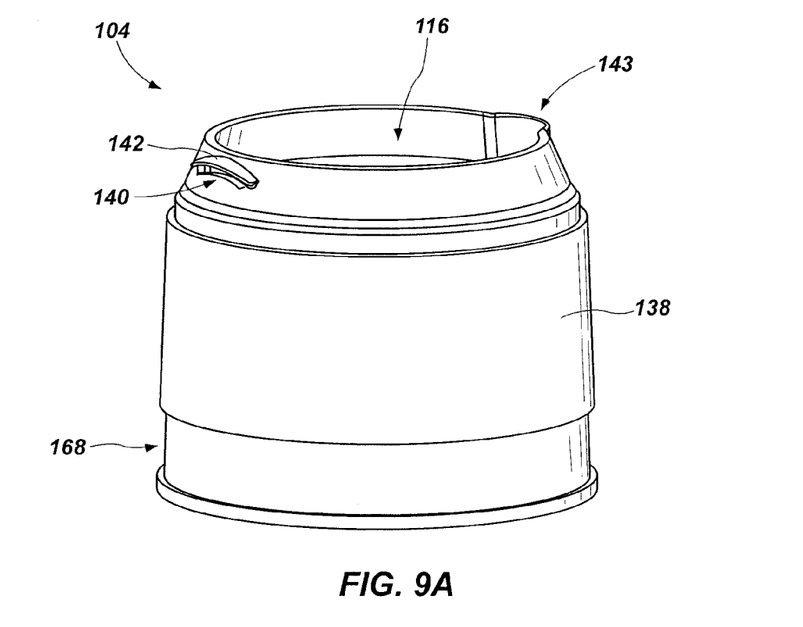
Figure 9B:
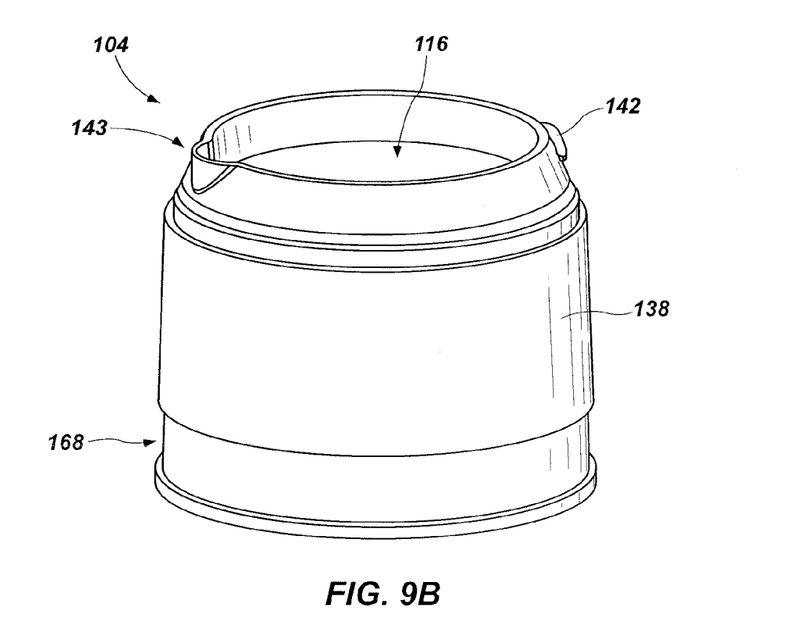

The liquid reservoir 104 is shown separately from the other components of the diffuser 100 in FIGS. 9A and 9B. As shown therein, the liquid reservoir 104 may further include a shroud member 142 extending laterally from the exterior sidewall 138 of the liquid reservoir 104 over the aperture 140 extending through the exterior sidewall 138. The shroud member 142 may be sized and configured to prevent liquid condensing on interior surfaces of the spout 106 from falling through the aperture 140 and into the space between the base member 102 and the liquid reservoir 104. In some embodiments, the aperture 140 may be elongated in the horizontal direction, and may be arcuate and curved downward. The shroud member 142 may be arcuate, and curved downward in similar fashion. The shroud member 142 may be located immediately above the aperture 140 as shown in FIG. 9A.

The liquid reservoir 104 may also include a liquid spout 143 located and configured for pouring liquid out from the receptacle 116 as needed after use of the diffuser 100.

As also shown in FIGS. 2A and 3, the diffuser 100 may include a heat sink 132. The heat sink 132 may comprise a metal body shaped and configured to draw heat away from other active, heat-generating components of the diffuser 100, such as the fan 130, the ultrasonic transducer 126, and a lighting system, which is described in further detail below. The heat sink 132 may be mounted to the base member 102 vertically above the fan 130.

Figure 4:
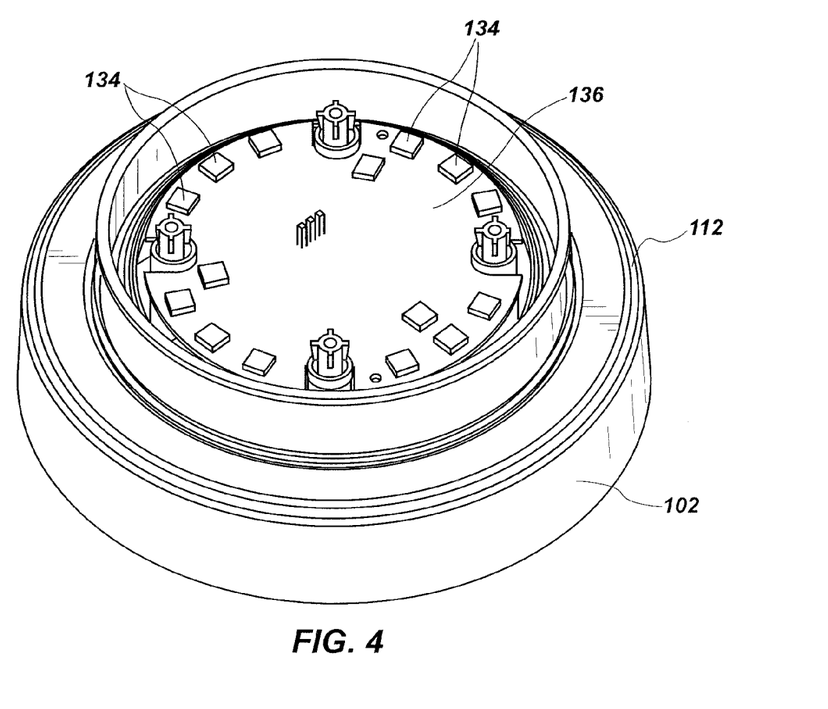
Figure 5:
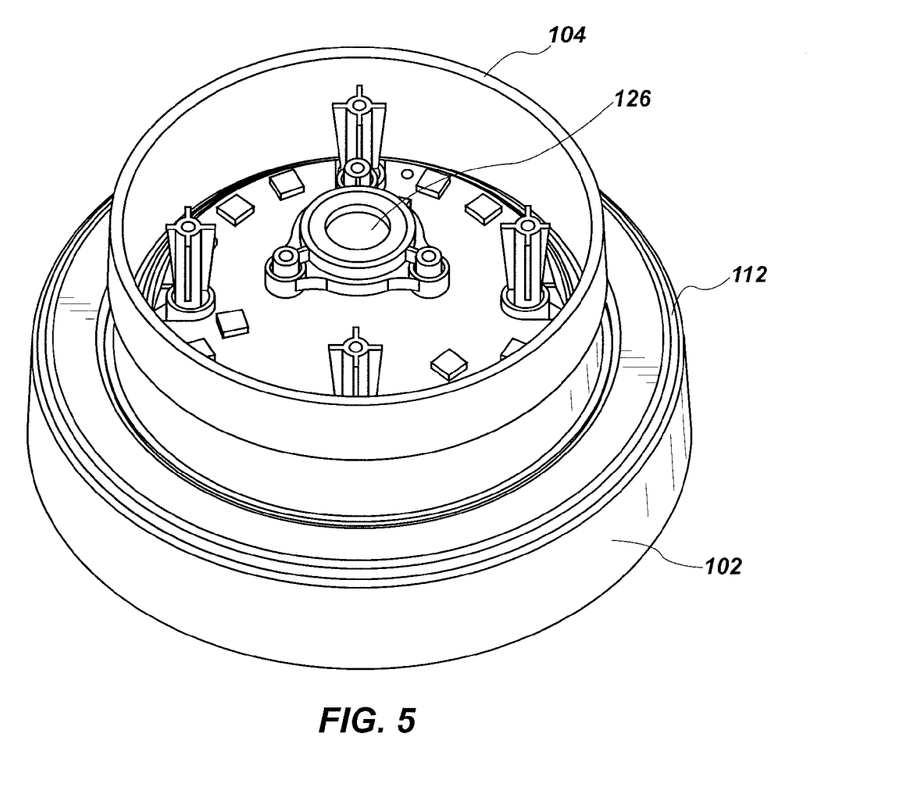
Figure 6:
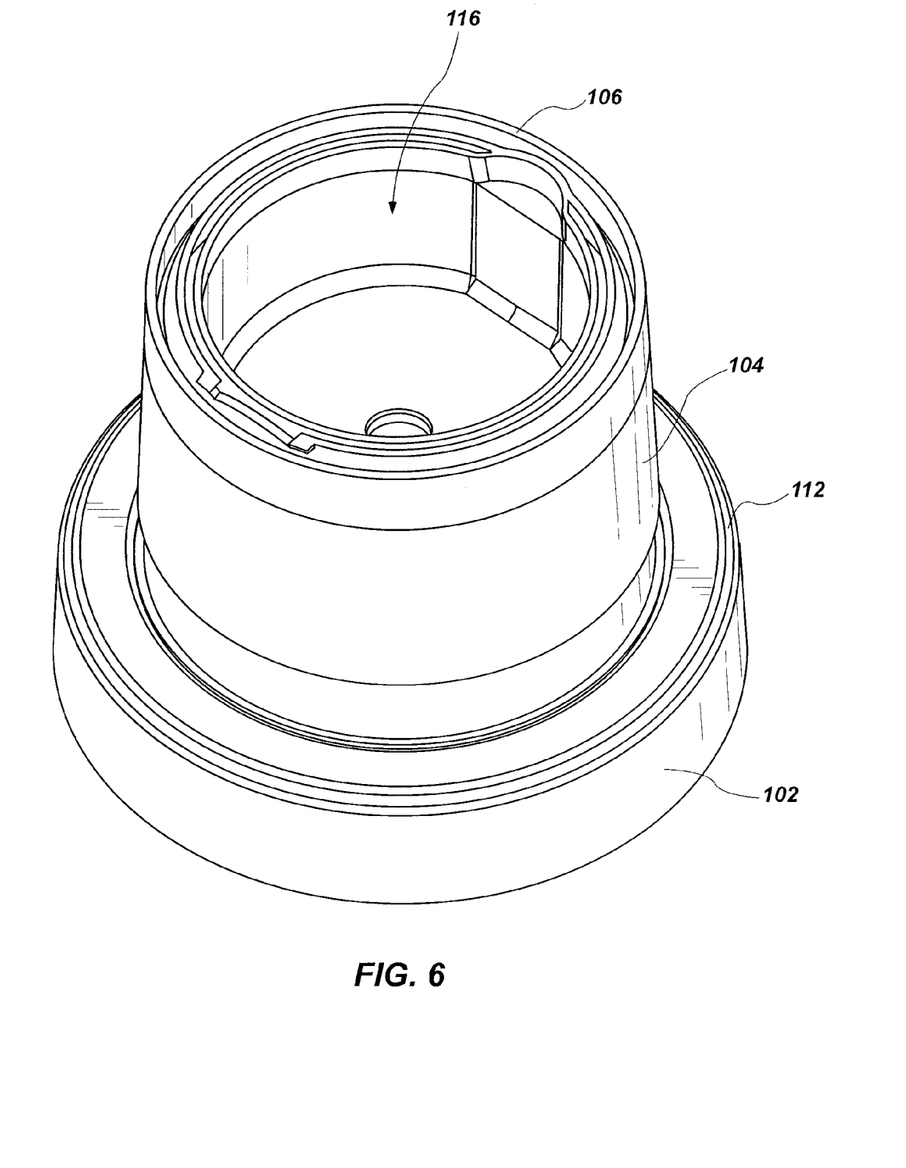

The diffuser 100 may include a lighting system. The lighting system may comprise one or more light-emitting diodes (LEDs) 134. The LEDs 134 may be used to generate light that may be visible from the exterior of the diffuser 100. In some embodiments, the one or more LEDs 134 may be disposed between the base member 102 and the liquid reservoir 104. For example, as shown in FIGS. 2A and 4, a printed circuit board 136 having a plurality of LEDs 134 mounted thereon may be mounted on the base member 102 vertically over the heat sink 132 and fan 130, and underneath the liquid reservoir 104. In some embodiments, the liquid reservoir 104 and the spout 106 may be at least substantially transparent, or at least substantially translucent to the light emitted by the LEDs 134, such that light emitted by the LEDs can pass through the liquid reservoir 104 and the spout 106.

In some embodiments, the LEDs 134 may be capable of emitting two or more colors of light. For example, a user may be able to select whether the light emitted by the LEDs is white, orange, red, green, blue, or purple. In one operational mode, the LEDs may emit a single selected color. In another operational mode, the LEDs may cycle through the various colors of light emitting each color for a duration of time, such as a few seconds or more, or a few minutes or more.

Referring again to FIG. 2A, the spout 106 may include an outer sidewall 144 configured to rest upon the liquid reservoir 104. In particular, the lower end of the outer sidewall 144 of the spout 106 may rest upon a shoulder formed toward the upper end of the exterior sidewall 138 of the liquid reservoir 104. An annular laterally-projecting ridge may be formed on one or both of the abutting surfaces of the outer sidewall 144 of the spout 106 and the exterior sidewall 138 of the liquid reservoir 104, so as to provide an interference fit therebetween and provide a substantially air-tight seal therebetween so as to prevent airflow generated from the fan from escaping laterally out from the diffuser 100 at the interface between the spout 106 and the liquid reservoir 104. The outer sidewall 144 of the spout 106 and the exterior sidewall 138 of the liquid reservoir 104 may be sized and configured such that the exterior surfaces thereof are smooth and continuous across the interface therebetween. The spout 106 may further include an interior vertical baffle wall 146 extending between an upper end 148 and a lower end 150 thereof. The upper end 148 of the baffle wall 146 may adjoin an interior surface of the outer sidewall 144 of the spout 106. When the spout 106 is positioned on the liquid reservoir 104 as shown in FIG. 2A, the lower end 150 of the baffle wall 146 may be positioned vertically over the receptacle 116 of the liquid reservoir 104 such that liquid condensing on interior surfaces of the spout 106 will drain down an interior side surface of the baffle wall 146 and fall back into the receptacle 116 of the liquid reservoir 104.

Figure 10A:
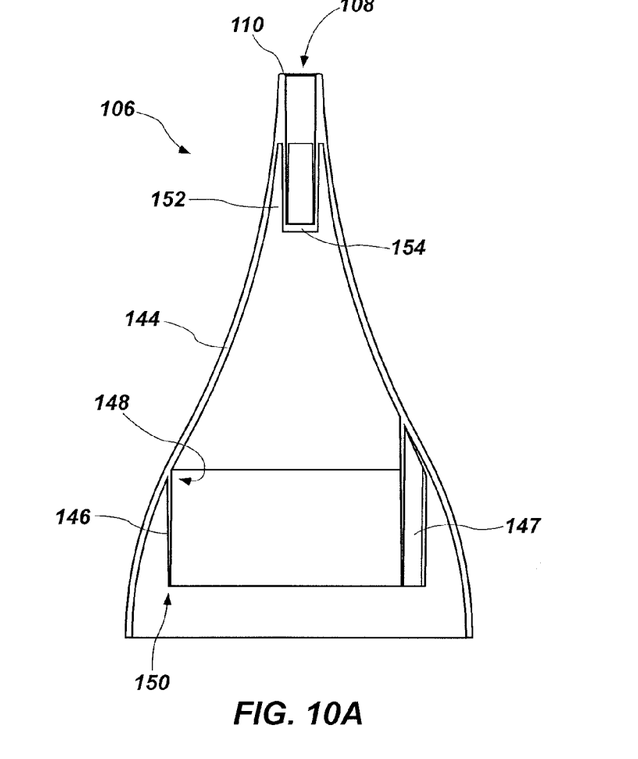
Figure 10B:
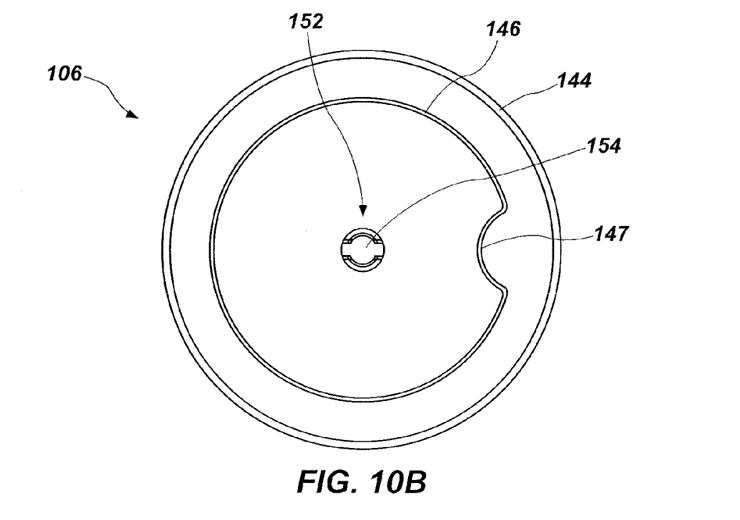

The spout 106 is shown separately from the other components of the diffuser 100 in FIGS. 10A and 10B. As shown therein, the spout 106 may further include a splash guard 152 located within the spout 106 proximate the opening 108 at the upper end 110 thereof. The splash guard 152 may be configured to prevent fluid held within the receptacle 116 of the liquid reservoir 104 from splashing out from the diffuser 100 through the opening 108 at the upper end 110 thereof. In particular, during operation of the diffuser 100, the ultrasonic vibrations generated within the liquid by the ultrasonic transducer 126 may cause splashing of the liquid, and the splash guard 152 may retain the splashing liquid within the space enclosed by the spout 106 and the liquid reservoir 104 over the bath of liquid held in the receptacle 116.

The splash guard 152 may include a lower surface 154 oriented at least substantially transverse to a longitudinal axis of the spout 106. In some embodiments, the lower surface 154 of the splash guard 152 may be located a distance D from the upper end 110 of the spout 106. For example, the distance D may be, for example, between about 1.5 inches and about 2.0 inches from the upper end 110 of the spout 106. The lower surface 154 of the splash guard 152 may have a width $W_{SG}$ (FIG. 2A) in a plane transverse to the longitudinal axis of the spout 106 that is greater than or equal to a maximum width $W_{OP}$ (FIG. 2A) of the opening 108 at the upper end 110 of the spout 106 in a plane transverse to the longitudinal axis of the spout 106. The opening 108 may have a maximum width $W_{OP}$ (e.g., a diameter) of, for example, between about 0.25 inch and about 0.75 inch (e.g., about 0.313 inch).

As shown in FIGS. 10A and 10B, the baffle wall 146 may be generally cylindrical, but may include a portion 147 that curves radially inwardly so as to form a recess in the cylindrical profile of the baffle wall 146. This recess may facilitate airflow passing through the diffuser 100 generated by the fan 130. In particular, the recess may facilitate the passage of the airflow between the liquid reservoir 104 and the spout 106 so as to allow the flowing air to enter the space enclosed by the liquid reservoir 104 and the spout 106 in the region overlying the liquid held within the receptacle 116.

Referring again to FIG. 2A, the portion 118 of the upper surface 112 of the base member 102 that extends laterally beyond the outer peripheral side surface 120 of the liquid reservoir 104 may be disposed at a lower elevation relative to portions 119 of the upper surface 112 of the base member 102 that are disposed within the liquid reservoir 104. This configuration reduces the risk of liquid that might unintentionally drip or fall down the exterior surface of the spout 106 and the liquid reservoir 104 from entering into the interior of the liquid reservoir 104 and contacting the various active and electronic components of the diffuser 100. Furthermore, the lower end of the exterior sidewall 138 of the liquid reservoir 104 may be disposed in an annular recess formed in the upper surface 112 of the base member 102, and an elastomeric seal ring may be disposed in the recess and between the upper surface 112 of the base member 102 and the exterior sidewall 138 of the liquid reservoir 104 to establish an at least substantially air- and liquid-tight seal therebetween, which may further reduce the risk of liquid from entering into the interior of the liquid reservoir 104 from the exterior thereof and contacting the various active and electronic components of the diffuser 100.

Figure 1:
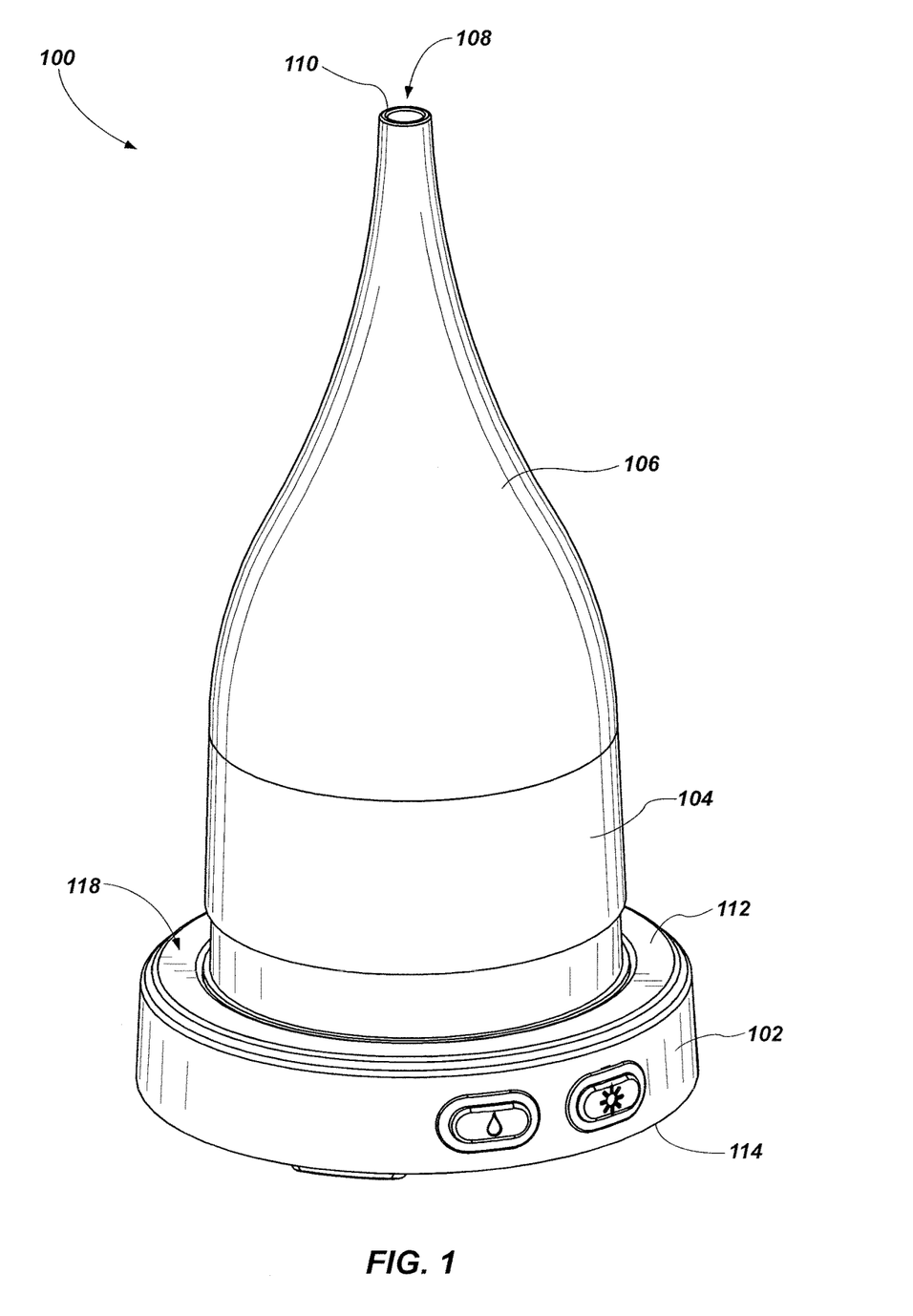
Figure 2B:
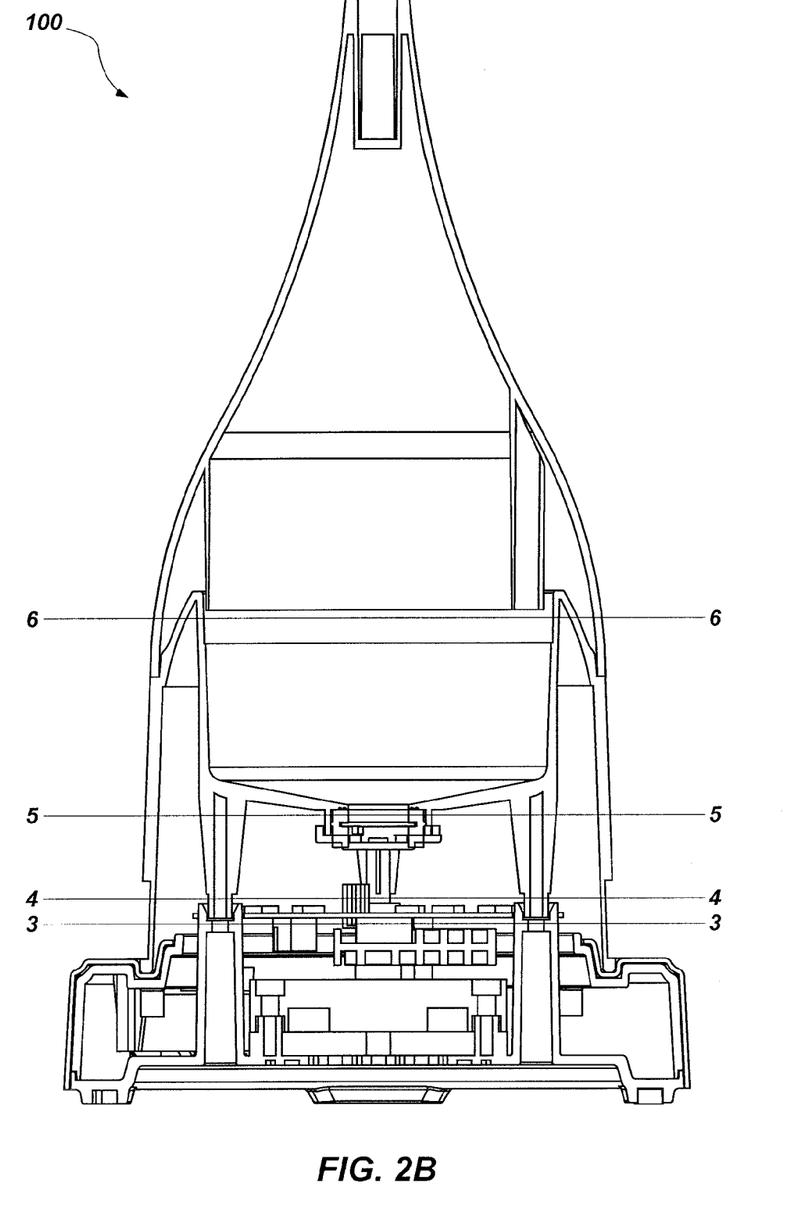
Figure 7:
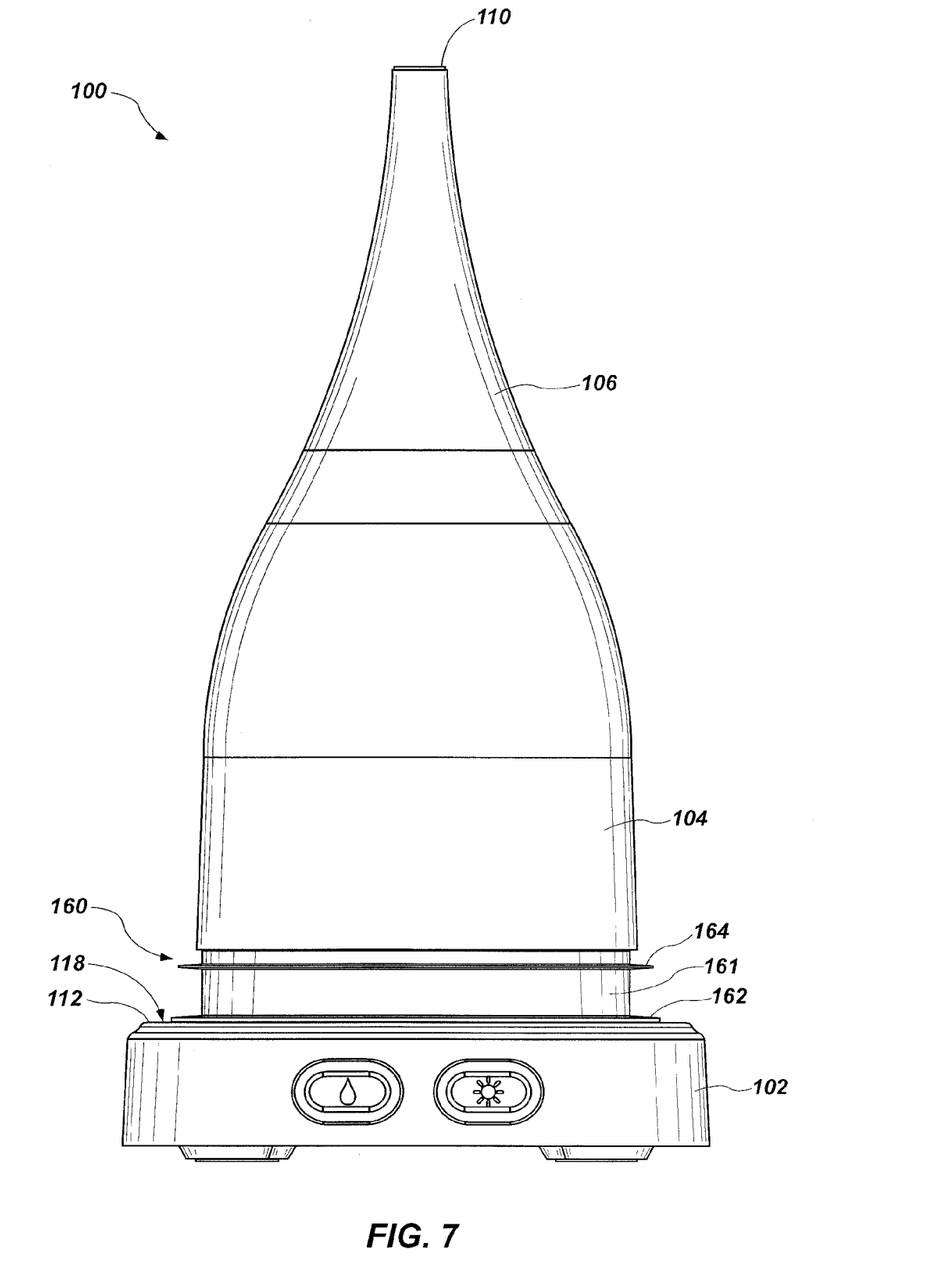
Figure 8A:
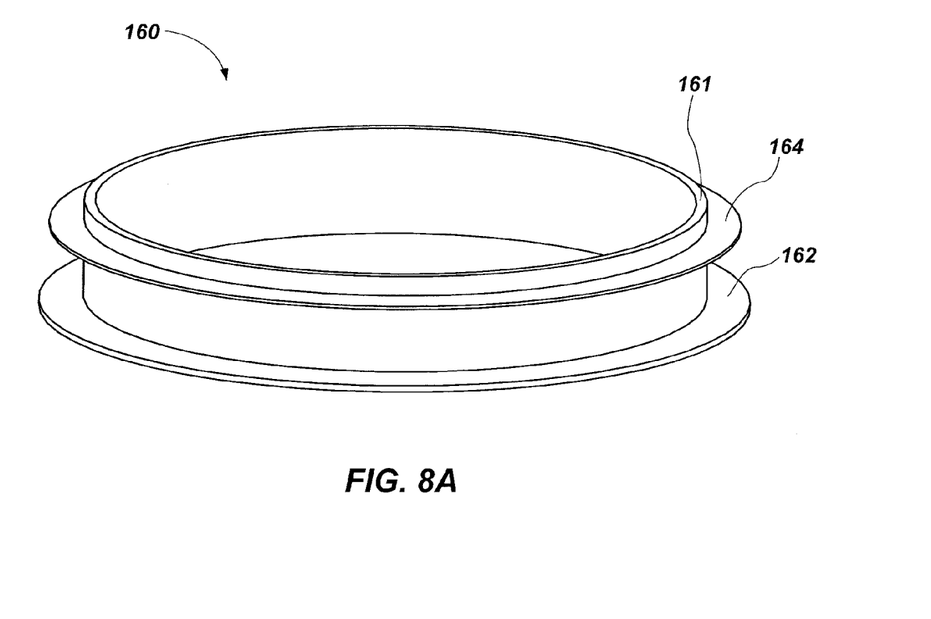
Figure 8B:
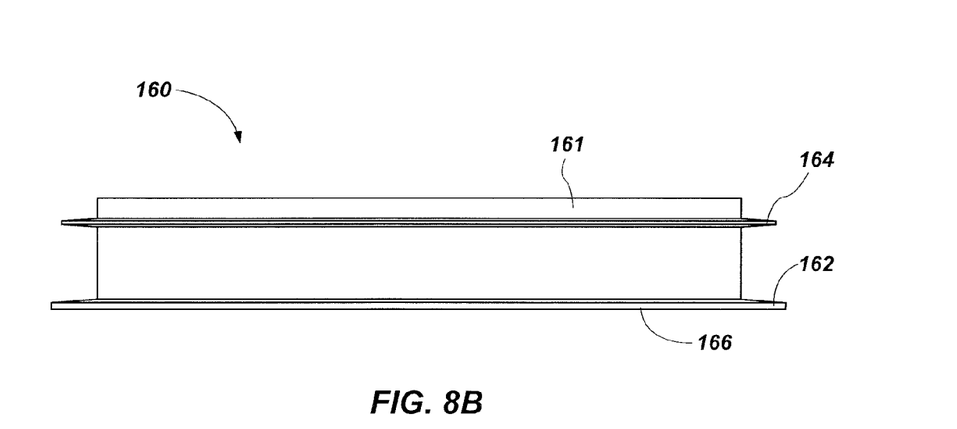

FIG. 7 is a front side view of the diffuser 100 and illustrates a polymeric gasket 160 of the diffuser 100 positioned thereon. The polymeric gasket 160 is not illustrated in FIGS. 1, 2A, and 2B. The polymeric gasket 160 is also shown in FIGS. 8A and 8B separate from the other components of the diffuser 100. The polymeric gasket 160 may comprise an elastomeric gasket that is at least substantially formed of and comprises an elastomeric polymer, such as silicone, although the gasket 160 may be formed from and comprise other elastomeric materials in additional embodiments. As shown in FIG. 7, the polymeric gasket 160 encircles the liquid reservoir 104 about the lower region of the exterior sidewall 138 of the liquid reservoir 104. As shown in FIGS. 8A and 8B, the polymeric gasket 160 includes a cylindrical wall 161, a first lower flange 162, and a second upper flange 164. In additional embodiments, the polymeric gasket 160 may include only one flange, or the polymeric gasket 160 may include more than two flanges.

Referring to FIG. 8B, the lower flange 162 may extend laterally from the bottom of the cylindrical wall 161, and a lower surface 166 of the lower flange 162 may define a bottom surface of the gasket 160. The lower surface 166 may be at least substantially planar, and may be configured to rest upon the portion 118 of the upper surface 112 of the base member 102 that extends laterally beyond the outer peripheral side surface 120 of the liquid reservoir 104 when the gasket 160 is positioned around the liquid reservoir 104 and on the base member 102, as shown in FIG. 7. Thus, when the gasket 160 is positioned around the liquid reservoir 104 and on the base member 102, the lower flange 162 extends at least partially over the portion 118 of the upper surface 112 of the base member 102 that extends laterally beyond the outer peripheral side surface 120 of the liquid reservoir 104.

Referring again to FIG. 8B, in some embodiments, an upper surface of the lower flange 162 may taper downward toward the lower surface 166 of the lower flange 162 in the direction extending laterally outward away from the cylindrical wall 161 of the gasket 160. The upper flange 164 may extend radially outward from the cylindrical wall 161 from an intermediate location between the upper and lower ends of the cylindrical wall 161. In some embodiments, the upper flange 164 may extend radially outward from the cylindrical wall 161 at a location in the upper half of the cylindrical wall 161 between the horizontal centerline and the upper end of the cylindrical wall 161, as shown in FIG. 8B. In some embodiments, the upper flange 164 may be tapered in the radial direction. For example, one or both of the upper and lower surfaces of the upper flange 164 may be tapered, and may taper toward one another in the direction extending laterally outward away from the cylindrical wall 161 of the gasket 160, as shown in FIG. 8B.

As shown in FIG. 2A, an annular recess 168 may be formed in the outer peripheral side surface 120 of the liquid reservoir 104. The annular recess 168 may have a height and depth that are substantially the same as, or slightly greater than, the height and width, respectively, of the cylindrical wall 161. Thus, the cylindrical wall 161 of the gasket 160 may rest at least substantially entirely within the annular recess 168 in the outer peripheral side surface 120 of the liquid reservoir 104 when the gasket 160 is positioned around the liquid reservoir 104 and on the base member 102.

In some embodiments, the polymeric gasket 160 may be at least partially transparent (e.g., translucent) to the light emitted by the one or more LEDs 134 so that the light emitted by the LEDs 134 is visible through the gasket 160.

Figure 11:
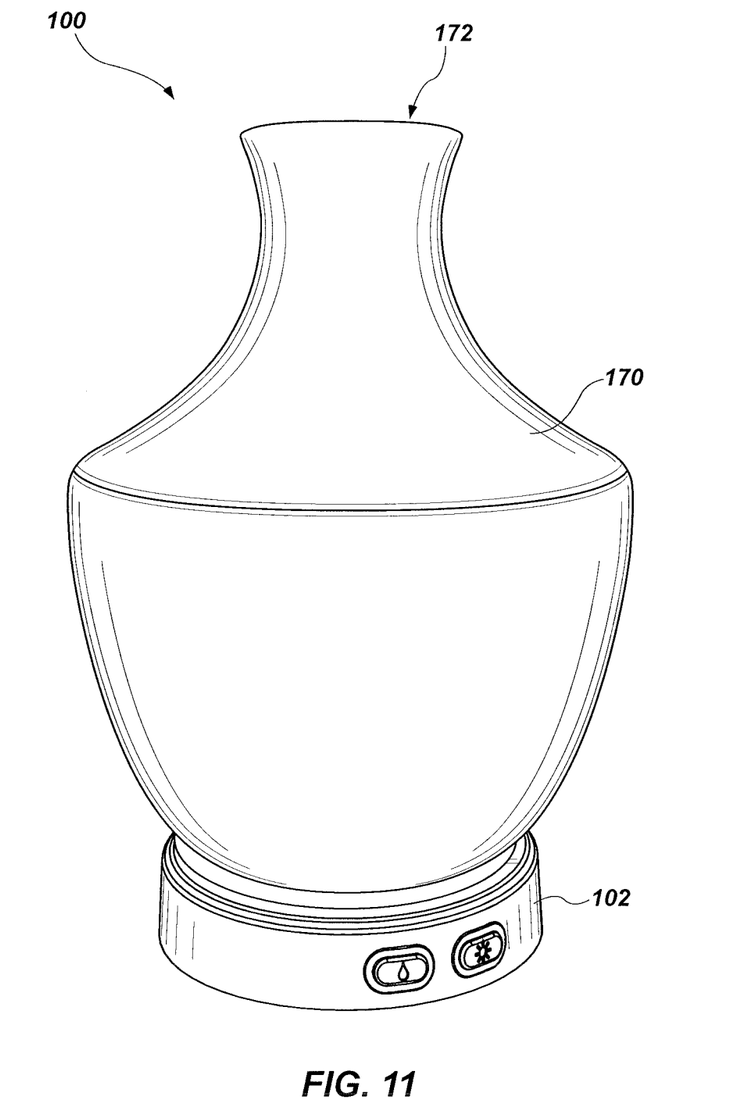

Referring to FIG. 11, the diffuser 100 may further include a removable decorative cover 170 that is sized and configured to be positioned over and around the liquid reservoir 104 and the spout 106 (FIG. 1), and to rest upon the lower flange 162 of the polymeric gasket 160 over the base member 102 (FIG. 7). The lower flange 162 of the gasket 160 is disposed between the cover 170 and the portion 118 of the upper surface 112 of the base member 102 that extends laterally beyond the outer peripheral side surface 120 of the liquid reservoir 104. The cover 170 includes an opening at an upper end 172 thereof such that the forced airflow generated by the fan 130 passes through the opening at the upper end 172 of the cover 170.

During operation of the diffuser 100, the light emitted by the LEDs 134 (FIG. 2A) may be visible through the opening at the upper end 172 of the cover 170. In addition, as previously mentioned, the gasket 160 may also be transparent or translucent to the light emitted by the LEDs 134, and the light emitted by the LEDs may be visible through the lower flange 162 of the gasket 160 at the interface between the cover 170 and the upper surface 112 of the base member 102 so as to provide a visible ring of light around the base of the cover 170 during operation of the diffuser 100.

The diffuser 100 is configured so as to operate with or without a decorative cover 170 thereon, and the airflow through the diffuser 100 is not affected by the presence or absence of a decorative cover 170 resting on the base member 102. In other words, the interior surfaces of the decorative cover 170 do not define any passageway for the forced airflow through the diffuser 100 generated by the fan 130.

In some embodiments, the diffuser 100 may be part of a kit that includes the base member 102, the liquid reservoir 104, and the spout 106 (with the various other components mounted therein and described with reference to FIGS. 2A, 2B, 3 through 7, 8A, and 8B), as well as two or more decorative covers 170 having different aesthetic appearances. The two or more decorative covers may be interchangeable on the diffuser 100 so as to allow a user to alter a decorative appearance of the diffuser 100.

While the present invention has been described herein with respect to certain embodiments, those of ordinary skill in the art will recognize and appreciate that it is not so limited. Rather, many additions, deletions, and modifications to the embodiments depicted and described herein may be made without departing from the scope of the invention as hereinafter claimed, and legal equivalents. In addition, features from one embodiment may be combined with features of another embodiment while still being encompassed within the scope of the invention as contemplated by the inventor. Further, the invention has utility in diffusers having different designs and configurations than those shown and described herein.

What is claimed is:

1. A diffuser for diffusing liquid into surrounding ambient air, comprising:
    a base member having an upper surface and a lower surface;
    an ultrasonic transducer mounted to the base member over the upper surface thereof;
    a liquid reservoir mounted to the base member over the upper surface thereof, the liquid reservoir having surfaces defining a receptacle for holding a volume of liquid therein, at least a portion of an upper surface of the base member extending laterally beyond an outer peripheral side surface of the liquid reservoir, the liquid reservoir including a bottom wall, at least one vertically extending sidewall, and an exterior sidewall extending upwardly from the base member and adjoining an upper end of the at least one vertically extending sidewall, the exterior sidewall having at least one aperture extending therethrough, at least a surface of the ultrasonic transducer exposed to any volume of liquid held within the receptacle such that ultrasonic vibrations of the ultrasonic transducer generate atomized droplets of the liquid over the volume of liquid held within the reservoir;
    a spout sized and configured to rest upon the liquid reservoir and including an opening at an upper end thereof;
    a fan mounted to the base member and configured to force airflow from the exterior of the diffuser, into the base member, around the receptacle in the liquid reservoir, through the at least one aperture, into a volume of space enclosed by the spout and the liquid reservoir overlying any volume of liquid held within the receptacle, and out through the opening at the upper end of the spout to the ambient air external the diffuser, the forced airflow carrying the atomized droplets of the liquid generated by the ultrasonic transducer to the exterior of the diffuser through the opening at the upper end of the spout;
    a polymeric gasket encircling the liquid reservoir and including at least one flange, the at least one flange extending at least partially over the portion of the upper surface of the base member extending laterally beyond the outer peripheral side surface of the liquid reservoir; and
    a cover sized and configured to be positioned over and around the liquid reservoir and the spout, and to rest upon the at least one flange of the polymeric gasket such that the at least one flange is disposed between the cover and the portion of the upper surface of the base member extending laterally beyond the outer peripheral side surface of the liquid reservoir, the cover including at least one opening at an upper end thereof such that the forced airflow generated by the fan passes through the opening at the upper end of the cover.

2. The diffuser of claim 1, wherein the polymeric gasket comprises an elastomeric gasket.

3. The diffuser of claim 2, wherein the elastomeric gasket comprises a silicone gasket.

4. The diffuser of claim 1, further comprising at least one light-emitting diode (LED) disposed between the base member and the liquid reservoir, wherein light emitted by the at least one LED is visible from the exterior of the diffuser.

5. The diffuser of claim 4, wherein the light emitted by the at least one LED is visible through the opening at the upper end of the cover.

6. The diffuser of claim 4, wherein the polymeric gasket is at least partially transparent to the light emitted by the at least one LED, the light emitted by the at least one LED being visible through the at least one flange of the polymeric gasket at an interface between the cover and the upper surface of the base member.

7. The diffuser of claim 4, wherein the at least one LED comprises a plurality of LEDs capable of emitting two or more colors of light.

8. The diffuser of claim 1, wherein the spout includes an outer sidewall configured to rest upon the liquid reservoir and an interior vertical baffle wall having an upper end and a lower end, the upper end of the baffle wall adjoining an interior surface of the outer sidewall of the spout, the lower end of the baffle wall positioned vertically over the receptacle of the liquid reservoir such that liquid condensing on interior surfaces of the spout will drain down an interior side surface of the baffle wall and fall back into the liquid reservoir.

9. The diffuser of claim 1, wherein the liquid reservoir further includes a shroud member extending from the exterior sidewall over the at least one aperture extending therethrough, the shroud member sized and configured to prevent liquid condensing on interior surfaces of the spout from falling through the at least one aperture and into the space between the base member and the liquid reservoir.

10. The diffuser of claim 1, further comprising a polymeric seal member disposed between a lower end of the exterior sidewall of the liquid reservoir and the base member.

11. The diffuser of claim 1, wherein the cover is a decorative cover.

12. The diffuser of claim 11, further comprising an additional decorative cover having a different appearance from the decorative cover, the decorative cover and the additional decorative cover being interchangeable on the diffuser so as to allow a user alter a decorative appearance of the diffuser.

13. The diffuser of claim 11, wherein the spout further includes a splash guard located within the spout proximate the opening at the upper end thereof, the splash guard configured to prevent fluid held within the receptacle of the liquid reservoir from splashing out from the diffuser through the opening at the upper end thereof.

14. The diffuser of claim 13, wherein the splash guard includes a lower surface oriented at least substantially transverse to a longitudinal axis of the spout.

15. The diffuser of claim 14, wherein the lower surface of the splash guard is located between about 0.25 inch and about 0.75 inch from the upper end of the spout.

16. The diffuser of claim 15, wherein the lower surface of the splash guard has a width in a plane transverse to the longitudinal axis of the spout that is greater than or equal to a maximum width of the opening at the upper end of the spout in a plane transverse to the longitudinal axis of the spout.

17. A method of assembling a diffuser for diffusing liquid into surrounding ambient air, comprising:
providing a structure including:
a base member having an upper surface and a lower surface;
an ultrasonic transducer mounted to the base member over the upper surface thereof;
a liquid reservoir mounted to the base member over the upper surface thereof, the liquid reservoir having surfaces defining a receptacle for holding a volume of liquid therein, at least a portion of an upper surface of the base member extending laterally beyond an outer peripheral side surface of the liquid reservoir, the liquid reservoir including a bottom wall, at least one vertically extending sidewall, and an exterior sidewall extending upwardly from the base member and adjoining an upper end of the at least one vertically extending sidewall, the exterior sidewall having at least one aperture extending therethrough, at least a surface of the ultrasonic transducer exposed to any volume of liquid held within the receptacle such that ultrasonic vibrations of the ultrasonic transducer generate atomized droplets of the liquid over the volume of liquid held within the reservoir;
a fan mounted to the base member and configured to force airflow from the exterior of the diffuser, into the base member, around the receptacle in the liquid reservoir, through the at least one aperture, and into a volume of space enclosed by a spout and the liquid reservoir overlying any volume of liquid held within the receptacle, the forced airflow carrying the atomized droplets of the liquid generated by the ultrasonic transducer to the exterior of the diffuser; and
a polymeric gasket encircling the liquid reservoir and including at least one flange, the at least one flange extending at least partially over the portion of the upper surface of the base member extending laterally beyond the outer peripheral side surface of the liquid reservoir;

resting a spout upon the liquid reservoir, the spout including an opening at an upper end thereof and enclosing a volume of space between the spout and the liquid reservoir; and positioning a cover over and around the liquid reservoir and the spout and resting the spout upon the at least one flange of the polymeric gasket such that the at least one flange is disposed between the cover and the portion of the upper surface of the base member extending laterally beyond the outer peripheral side surface of the liquid reservoir, the cover including at least one opening at an upper end thereof such that the forced airflow generated by the fan passes through the opening at the upper end of the cover.

18. The method of claim 17, wherein the structure further comprises at least one light-emitting diode (LED) disposed between the base member and the liquid reservoir, and wherein the polymeric gasket is at least partially transparent to the light emitted by the at least one LED, the light emitted by the at least one LED being visible through the at least one flange of the polymeric gasket at an interface between the cover and the upper surface of the base member.

19. A method of using a diffuser for diffusing liquid into surrounding ambient air, comprising:

providing a diffuser, including:

a base member having an upper surface and a lower surface;

an ultrasonic transducer mounted to the base member over the upper surface thereof;

a liquid reservoir mounted to the base member over the upper surface thereof, the liquid reservoir having surfaces defining a receptacle for holding a volume of liquid therein, at least a portion of an upper surface of the base member extending laterally beyond an outer peripheral side surface of the liquid reservoir, the liquid reservoir including a bottom wall, at least one vertically extending sidewall, and an exterior sidewall extending upwardly from the base member and adjoining an upper end of the at least one vertically extending sidewall, the exterior sidewall having at least one aperture extending therethrough, at least a surface of the ultrasonic transducer exposed to any volume of liquid held within the receptacle;

a spout sized and configured to rest upon the liquid reservoir and including an opening at an upper end thereof;

a fan mounted to the base member;

a polymeric gasket encircling the liquid reservoir and including at least one flange, the at least one flange extending at least partially over the portion of the upper surface of the base member extending laterally beyond the outer peripheral side surface of the liquid reservoir; and a cover including at least one opening at an upper end thereof;

providing a volume of liquid in the receptacle of the liquid reservoir;

resting the spout upon the liquid reservoir;

positioning the cover over and around the liquid reservoir and the spout and resting the spout upon the at least one flange of the polymeric gasket such that the at least one flange is disposed between the cover and the portion of the upper surface of the base member extending laterally beyond the outer peripheral side surface of the liquid reservoir;

supplying power to the ultrasonic transducer and generating atomized droplets of the liquid over the volume of liquid held within the reservoir by ultrasonic vibrations of the ultrasonic transducer;

supplying power to the fan such that the fan forces airflow from the exterior of the diffuser, into the base member, around the receptacle in the liquid reservoir, through the at least one aperture, into a volume of space enclosed by the spout and the liquid reservoir overlying the volume of liquid held within the receptacle, and out through the opening at the upper end of the spout to the ambient air external the diffuser, the forced airflow carrying the atomized droplets of the liquid generated by the ultrasonic transducer to the exterior of the diffuser through the opening at the upper end of the spout.

\* \* \* \* \*